US00PP11625P

United States Patent [19]

Noodelijk

[11] Patent Number: Plant 11,625

[45] Date of Patent: Nov. 7, 2000

[54] CHRYSANTHEMUM PLANT NAMED 'XANTHUS'

[75] Inventor: Robert Noodelijk, Woubrugge, Netherlands

[73] Assignee: Chrysanthemum Breeders Association N.V., Netherlands

[21] Appl. No.: 09/179,454

[22] Filed: Oct. 27, 1998

[51] Int. Cl.[7] ..... A01H 5/00

[52] U.S. Cl. ..... Plt./295

[58] Field of Search ..... Plt./295

[56] References Cited

U.S. PATENT DOCUMENTS

P.P. 4,244 4/1978 Greinke ..... Plt./295
P.P. 6,591 2/1989 Sueptitz ..... Plt./295

*Primary Examiner*—Howard J. Locker
*Attorney, Agent, or Firm*—Parkhurst & Wendel, L.L.P.

[57] ABSTRACT

A chrysanthemum plant named Xanthus characterized by its medium sized blooms with yellow ray and disc florets and mounding prolific branching; early natural season flower date of August 1–4; blooming for a period of 5 weeks.

2 Drawing Sheets

BACKGROUND OF THE INVENTION

The new plant of the present invention comprises a new and distinct cultivar of chrysanthemum plant that is a cross of unknown *Dendranthema grandiflora* parents. The new and distinct cultivar was a seedling resulting from the open pollination among groups of chrysanthemum cultivars maintained under the control of the inventor for breeding purposes. The new and distinct cultivar was discovered and selected as one flowering plant by Rob Noodelijk on a cultivated field in Rijsenhout, Holland in August, 1996. The plant has been asexually reproduced by cuttings in greenhouses at Rijsenhout, Holland. The new cultivar has been found to retain its distinctive characteristics through successive propagations.

SUMMARY OF THE INVENTION

The present invention is a new and distinct variety of chrysanthemum of a medium sized bloom and yellow color.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
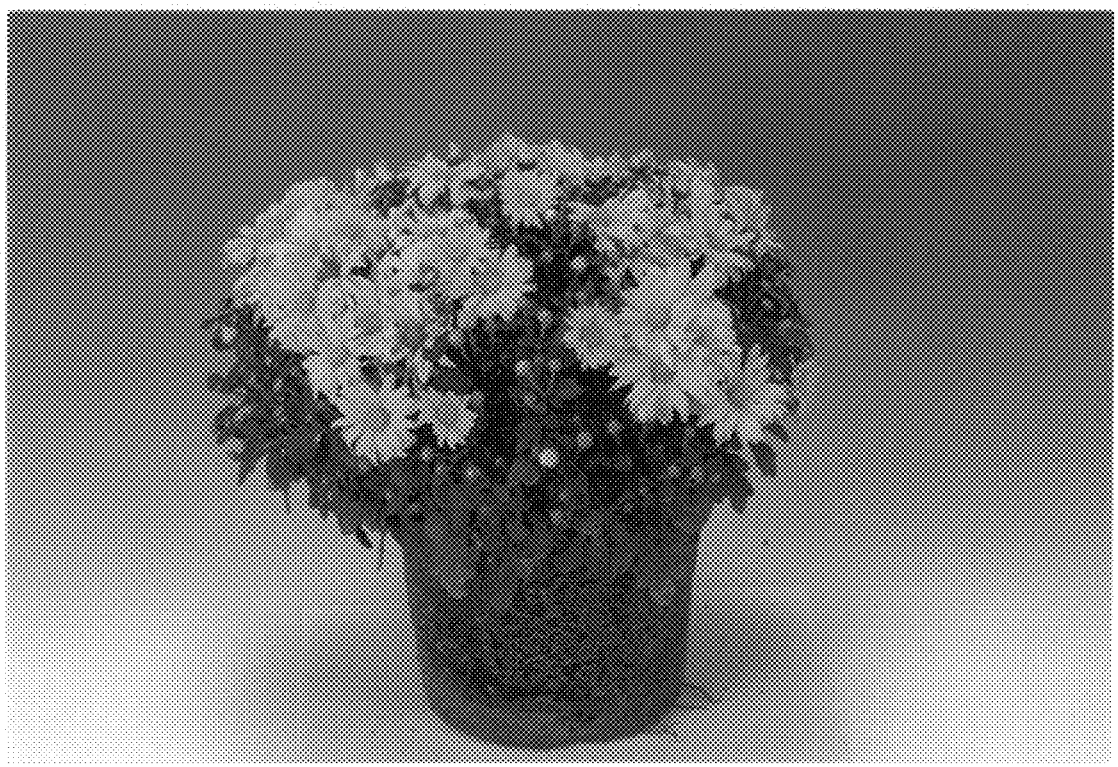
FIG. 1 shows a plant of the cultivar in various stages of bloom.
Figure 2:
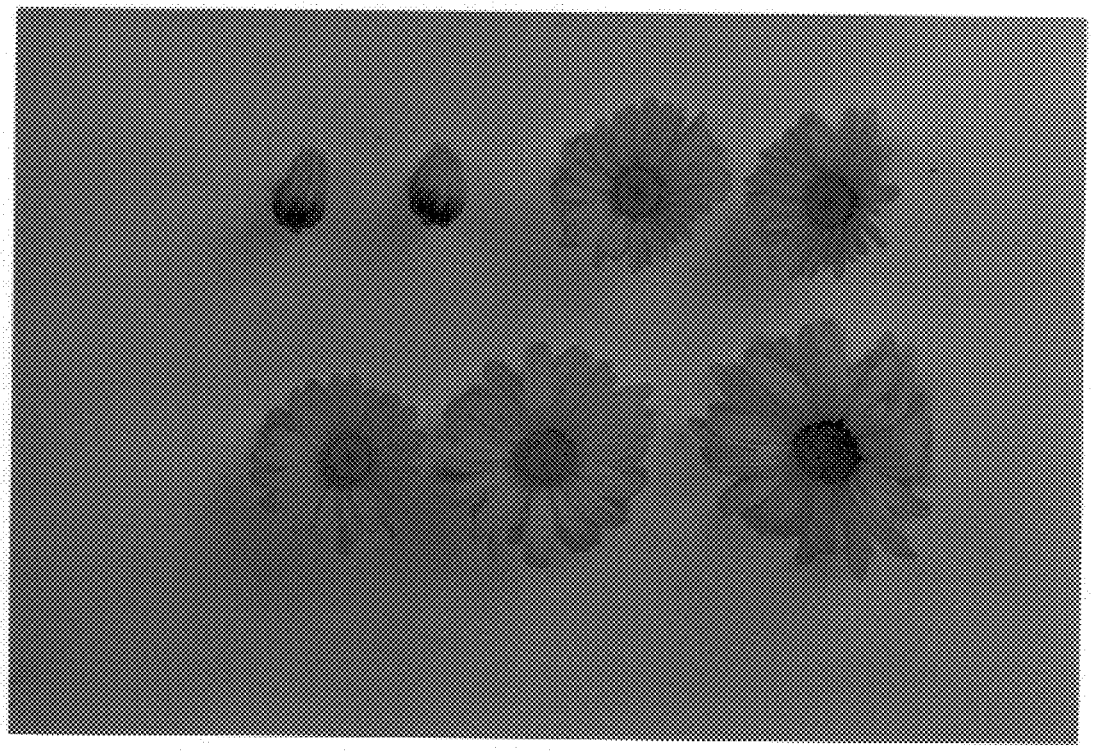
FIG. 2 shows the various stages of bloom of the new cultivar.
Figure 3:
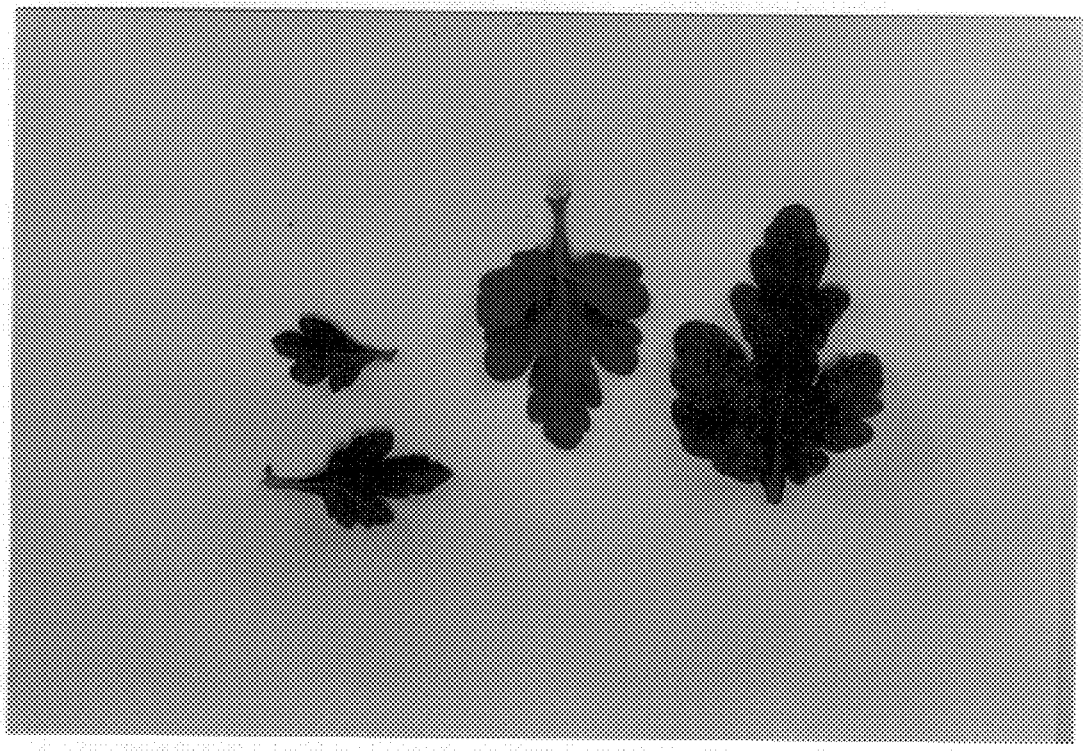
FIG. 3 shows foliage of the new cultivar.

This new variety of chrysanthemum is of the botanical classification *Dendranthema grandiflora*. The observations and measurements were gathered from plants grown outdoors in Rijsenhout, Holland under natural day length and temperature and planted week 22 in 1997 and 1998. The natural blooming date for this crop was August 1–4 (week 31). The average height of the plants was 20 cms. This new variety produces medium sized blooms with yellow ray and disc florets blooming for a period of 5 weeks.

The following is a description of the plant and characteristics that distinguish Xanthus as a new and distinct variety. The color designations (color designations are from the R.H.S. Colour Chart) are taken from the plant itself.

Accordingly, any discrepancies between the color designations and the colors depicted in the photographs are due to photographic tolerances.

| Botanical Classification CULTIVAR Xanthus | |
|---|---|
| Bud | |
| Size | MEDIUM<br>CROSS SECTION ± 1.3 CM<br>HEIGHT ± 1.5 CM |
| Outside Color | YELLOW 3 C |
| Bloom | |
| Size | MEDIUM |
| Fully Expanded | 5–6 CM |
| Borne (number of blooms per branch) | UPPER AND LOWER PORTION<br>PLURAL BLOOMS PER BRANCH<br>(APPROX. 6 BLOOMS) |
| -Length of lateral branch | FROM TOP TILL BOTTOM<br>APPROX. 11 CM |
| -Lateral branch, Attachment | MEDIUM |
| -Branching | Mounding and prolific with 8–10 breaks after pinching |
| Form | SINGLE(DAISY) |
| Performance (on the plant) | 5 WEEKS |
| Color | |
| Disc florets | At an early stage of inflorescence<br>Yellow 3 A |
| Color of the upper surface of the majority of the ray-florets | YELLOW 3 A |
| Color of the lower surface of the majority of the ray-florets | YELLOW 3 A |
| Tonality from Distance | A COMPACT GARDENMUM WITH YELLOW SINGLE FLOWERS |
| Discoloration of the ray florets | NONE |
| Discoloration of the disc florets | To Yellow 13 A |
| Pollen | YELLOW-ORANGE 14 A |
| Ray florets | |
| Texture | UPPERSIDE SMOOTH<br>UNDERSIDE SMOOTH |
| Number | ±23–26 |
| Cross-section | FLAT |
| Longitudinal axis of the majority | STRAIGHT |
| Shape of tip | DENTATE |
| Fragrance | TYPICAL CHRYSANTHEMUM |
| Disc Diameter | SMALL, 1 ½CM |

-continued

| Botanical Classification CULTIVAR Xanthus | |
|---|---|
| Reproductive Organs | |
| Stamen (present in disc florets) | YELLOW, THIN, ±4 MM IN LENGTH |
| Pollen | Present, abundant |
| Styles (present in both ray and disc florets) | YELLOW, TRIN |
| Style Length | ±4 MM |
| Stigmas | YELLOW |
| Stigma Width | ±1 MM |
| Ovaries | ENCLOSED IN CALYX |
| Plant | |
| Form | A GARDENMUM (POT MUM) MEANT FOR OUTDOOR USE |
| Growth | SHORT |
| Height (from soil level) | ±20 CM |
| Stem Color | NEAR GREEN 144 A |
| Stem Strength | STRONG |
| Stem Brittleness | PRESENT |
| Stem Anthocyanin Coloration | NONE |
| Natural blooming date | BEGINNING OF AUGUST (WEEK 31) |

-continued

| Botanical Classification CULTIVAR Xanthus | |
|---|---|
| Foliage | |
| Color | UPPERSIDE GREEN 137 A UNDERSIDE GREEN 147 B |
| Size | SMALL: LENGTH ± 7 CM WIDTH ± 5 CM |
| Quantity (number per lateral branch) | 14–16 |
| Shape | INCURVED |
| Texture | FLESHY |
| Ribs and Veins | RIBS AND VEINS NOT SO WELL DEVELOPED |
| Edge | LOBED |
| Shape of Base of Sinus Between Lateral Lobes | ROUND |
| Margin of Sinus Between Lateral Lobes | DIVERGING |
| Shape of Base | ASYMMETRIC |
| Apex | MUCRONATE |

I claim:

1. A new and distinct variety of chrysanthemum plant as described and illustrated.

* * * * *